United States Patent [19]

Neumann

[11] 4,145,421
[45] Mar. 20, 1979

[54] TREATING SPASTIC CONDITIONS
[75] Inventor: Peter Neumann, Berne, Switzerland
[73] Assignee: Sandoz Ltd., Basel, Switzerland
[21] Appl. No.: 898,558
[22] Filed: Apr. 21, 1978
[30] Foreign Application Priority Data
Apr. 22, 1977 [GB] United Kingdom ............... 16914/77
Apr. 22, 1977 [GB] United Kingdom ............... 16915/77
[51] Int. Cl.$^2$ ........................................... A61K 31/495
[52] U.S. Cl. .................................. 424/250; 424/251;
424/258; 424/271; 424/272
[58] Field of Search ........................................ 424/250

[56] References Cited
FOREIGN PATENT DOCUMENTS
1381979 1/1975 United Kingdom.

Primary Examiner—Stanley J. Friedman
Attorney, Agent, or Firm—Gerald D. Sharkin; Richard E. Vila; Joseph J. Borovian

[57] ABSTRACT

This invention provides a new myotonolytic use of thiazoline, oxazoline and imidazoline derivatives and novel pharmaceutical compositions for such use.

6 Claims, No Drawings

TREATING SPASTIC CONDITIONS

IMPROVEMENTS IN OR RELATING TO ORGANIC COMPOUNDS

The present invention relates to a novel pharmaceutical use of thiazoline, oxazoline and imidazoline derivatives of formula I,

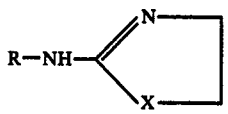

wherein either (i) X is sulphur or oxygen and R is a radical of formula II,

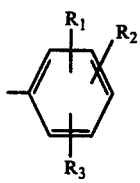

wherein each of $R_1$, $R_2$ and $R_3$, independently, is hydrogen, halogen, alkyl, alkoxy, nitro, cyano, hydroxy or alkylthio, or (ii) X is imino and R is a radical of formula III,

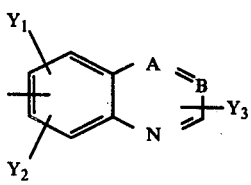

wherein either each of A and B is =CH—, or one of A and B is =CH— and the other of A and B is =N—, $Y_1$ and $Y_2$, independently, are hydrogen, halogen, alkyl, alkoxy, nitro, trifluoromethyl, cyano, hydroxy or alkylthio, and $Y_3$ is hydrogen, alkyl or alkoxy, and novel pharmaceutical compositions containing a compound of formula I as an active ingredient.

The compounds of formula I are, in general, known from e.g. French Pat. No. 1,313,055 and U.K. Patent specification No. 1,381,479 and said to be active as antihypertensives.

The compounds now have been found to be useful as myotonolytics, for example for the treatment of spastic conditions of different etiology (neurological, inflammatory, rheumatic, etc.) and muscle relaxants, as indicated by standard tests. For example, in rabbits on i.v. administration of from 0.0002 to 0.1 mg/kg animal body weight of the compounds a significant muscle relaxing effect is observed in accordance with the method of Teschendorf et al, Arch. Exp. Pharmacol. 266, 467–468 (1970).

Preferably any carbon containing substituent has up to 4 carbon atoms, especially 2 or more, especially 1 carbon atom.

Halogen is preferably fluorine, chlorine or especially bromine.

Preferred examples of formula I, where R is a radical of formula II, are those where X is oxygen, $R_3$ is hydrogen and $R_1$ and $R_2$ are chosen form hydrogen, halogen or alkyl, especially 2-(2,6-dimethylanilino)-2-oxazoline and 2-(2-chloro-6-methylanilino)-2-oxazoline.

Preferred examples of formula I, where R is a radical of formula III, are those compounds wherein $Y_1$ is halogen, especially chlorine or bromine, and $Y_2$ and $Y_3$ are hydrogen, e.g. 5-bromo- and 5-chloro-6-(2-imidazolin-2-yl-amino)-quinolines and -quinoxalines and 8-bromo-7-(2-imidazolin-2-yl-amino)-quinazoline and -quinoline.

Other examples are those compounds of formula I specifically mentioned in the above-mentioned French Patent and U.K Patent Specification which are hereby incorporated by reference.

For the above-mentioned novel uses the dosage will, of course, vary depending on the compound employed, mode of administration and therapy desired. However, in general, satisfactory results are obtained with a daily dosage of from 0.0001 mg to about 1 mg per kg animal body weight, conveniently given in divided doses 2 to 4 times a day or in sustained release form. For the larger mammal, the total daily dosage is in the range from about 1 to about 10 mg, e.g. between 1 and 6, preferably between 1.5 and 3 mg.

However, it is especially preferred to use a pharmaceutical composition in unit dosage form comprising from 0.25 mg to 2 mg of a free base form of a compound of formula I as defined above, or an equivalent amount of a pharmaceutically acceptable acid addition salt form thereof, in association with a pharmaceutical carrier or diluent. Preferably the unit dosage form containing up to 1.8 mg, preferably up to 1.5 mg of the free base of a compound of formula I or the equivalent amount of pharmaceutically acceptable acid addition salt form.

As used herein the term "unit dosage form" refers both to solid and liquid dosage forms and refers generally to that quantity of composition in the final dosage form in question (i.e., compositions as administered), which is appropriate for administration of the required dosage of a compound of formula I.

The compositions may already be in the final form ready for administration, for example in the form of integral solid dosage forms, e.g. a tablet. The composition may be packaged to facilitate administration of a unit dosage form, e.g. an ampoule containing a sterile injectable liquid. In the case of such forms the term "unit dosage forms" refers to the weight of compound of formula I in one such form and this, for example, may vary depending on the form in question.

The compositions may contain multiple unit dosages. For example a tablet may be formulated with a break line such that it may be broken into two halves. In such cases the term "unit dosage forms" refers to the weight of compound of formula I· in any portion thereof, adapted to be separated before administration.

The compositions may be in bulk form, e.g. when in the form of a liquid, a powder, or granules. Such forms may contain the compound of formula I in such a concentration that a conveniently administered portion recognized in the art, e.g. from 1 to 10 ml, e.g. a teaspoonful, contains the required dosage of compound of formula I. In such cases the term "unit dosage forms" refers to the weight of compound of formula I in such a portion. It will be appreciated that such concentrations may vary within wide limits, and it is possible that a concentrate of a compound of formula I could be formulated suitable for dilution to afford a "unit dosage form".

The present invention also include a package containing preferably the above defined unit dosage forms in physical relation to instructions for administration of a therapeutically effective amount of a compound of formula I as a myotonolytic or muscle relaxant.

As indicated above the compounds may be administered orally in the form of tablets, powders, granules, capsules, suspensions, sirups and elixirs, or parenterally in the form of injectable solutions or suspensions. Aside from the compound of formula I the compositions may contain pharmaceutically inert organic or inorganic adjuvants, optionally granulating agents, binding agents, lubricants, dispersing agents, wetting agents and preservatives. Moreover, the pharmaceutical compositions may contain colouring, flavouring and sweetening substances, etc. Adjuvants for the production of tablets may be calcium carbonate, lactose, microcrystalline cellulose, mannitol, or talc. Starch and alginic acid or microcrystalline cellulose may be used as granulating and disintegrating agents, starch, polyvinylpyrrolidone and gelatine may be used as binding agents, and magnesium stearate, stearic acid, colloidal silicon dioxide and talc as lubricants. Tablet formulations may be coated or uncoated, with the coating being applied in a manner per se and having the purpose of delaying the disintegration and adsorption in the gastrointestinal tract, thus providing a retarded effect over a longer period. Suitable suspending agents for the production of liquid administration forms are especially methyl cellulose, tragacanth and sodium alginate. Suitable wetting agents are e.g. polyoxyethylene stearate and polyoxyethylene sorbitan-monooleate. Furthermore, preservatives such as p-hydroxy-benzoic acid alkyl ester may be used. Capsule formulations may contain the compound of formula I on its own or together with an inert solid diluent, for example calcium phosphate, starch, lactose, mannitol, colloidal silicon dioxide and microcrystalline cellulose.

Solid preparations are preferred, especially hard-filled capsules and tablets, for reasons of easier production and favourable administration.

The compounds may be administered in free base form or in pharmaceutically acceptable acid addition salt form. Such salt forms are known and include for example the hydrochloride or tartrate. The free base forms and said acid addition salt forms exhibit the same order of activity.

The following Examples are illustrative of compositions for use in the invention.

EXAMPLE 1

Tablet or capsule suitable for oral administration

Tablets or capsules containing the ingredients indicated below may be prepared by conventional techniques and are useful in treating spastic conditions at a dose of one or two tablets four times a day, or one capsule two to four times a day.

| Ingredient | Tablet | Capsule |
|---|---|---|
| 2-(2,6-dimethylanilino)-2-oxazoline | 0.5 mg | 2 mg |
| Lactose | 70.6 mg | 173.5 mg |
| Microcrystalline cellulose | 18.0 mg | — |
| Corn starch | — | 120 mg |
| Colloidal silicon dioxide | 0.45 mg | 1.5 mg |
| Magnesium stearate | 0.45 mg | 3.0 mg |
| | 90 mg | 300 mg |

If desired the tablet may be shaped so that it may be easily divided into two.

EXAMPLE 2

Tablet or capsule suitable for oral administration

Tablets or capsules containing the ingredients indicated below may be prepared by conventional techniques and are useful in treating spastic conditions at a dose of one or two tablets four times a day or one capsule two to four times a day.

| Ingredient | Tablet | Capsule |
|---|---|---|
| 5-bromo-6-(2-imidazolin-2-yl-amino)-quinoxaline (tartrate) | 0.76 mg (~0.5 mg base) | 3 mg (~2 mg base) |
| Lactose | 70.34 mg | 172.5 mg |
| Microcrystalline cellulose | 18.0 mg | — |
| Corn starch | — | 120.0 mg |
| Colloidal silicon dioxide | 0.45 mg | 1.5 mg |
| Magnesium stearate | 0.45 mg | 3.0 mg |
| | 90 mg | 300 mg |

If desired the tablet may be shaped so that it may be easily divided into two.

EXAMPLE 3

Dragées suitable for oral administration

Dragées containing the ingredients indicated below may be prepared by conventional techniques and are useful in the treatment of spastic conditions when administered at a dose of one dragée two to four times a day.

| Ingredient | Weight | | |
|---|---|---|---|
| 2-(2,6-dimethylanilino)-2-oxazoline | 2 mg | — | |
| 5-bromo-6-(2-imidazolin-2-yl-amino)-quinoxaline (tartrate) | — | 2.28 mg | (~1.5 mg base) |
| Polyvinylpyrrolidone | 3.6 mg | 3.6 mg | |
| Lactose | 69.55 mg | 69.27 mg | |
| Magnesium stearate | 0.9 mg | 0.9 mg | |
| Colloidal silicon dioxide | 0.45 mg | 0.45 mg | |
| Corn starch | 13.5 mg | 13.5 mg | |
| Dragee mass | 100 mg | 100 mg | |
| | 190 mg | 190 mg | |

EXAMPLE 4

Sterile solution for injection

A solution for injection containing the ingredients indicated below may be prepared by conventional techniques including buffering as indicated below and subsequent sterilizing in conventional manner. The solution may be injected once a day in the treatment of spastic conditions.

| Ingredient | Weight or Volume | | |
|---|---|---|---|
| 2-(2,6-dimethylanilino)-2-oxazoline | 6 mg | — | |
| 5-bromo-6-(2-imidazolin-2-yl-amino)-quinoxaline (tartrate) | — | 9 mg | (~6.0 mg base) |
| Sodium chloride | q.s. | q.s. | |
| Distilled water | to 5 ml | to 5 ml | |
| Buffer to pH 5 | | | |

EXAMPLE 5

Elixir for oral administration

An elixir containing the ingredients indicated below may be prepared by conventional techniques, including buffering as indicated below. The elixir may be administered once or twice a day in 2 ml quantities for the treatment of spastic conditions.

| Ingredient | Weight | |
|---|---|---|
| 2-(2,6-dimethylanilino)-2-oxazoline or 5-bromo-6-(2-imidazolin-2-yl-amino)-quinoxaline in free base form | 0.075 | g |
| Glycerol | 10.0 | g |
| Tinctura Auranti dulcis | 10.0 | g |
| Saccharin | 0.02 | g |
| Karion F | 60.0 | g |
| Caramel-Sugar colouring | 0.05 | g |
| Ethyl alcohol pharm. | 15.0 | g |
| Citric acid to pH 5 | q.s. | |
| Dist. water | 100.0 | ml |

What we claim is:

1. A method of treating spastic conditions in animals or relaxing muscles in animals which comprises administering a therapeutically effective amount of a compound of formula I,

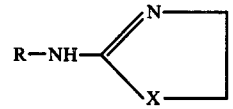

wherein X is imino and R is a radical of formula III,

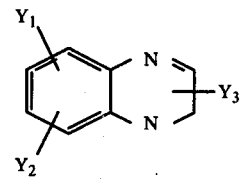

wherein,
$Y_1$ and $Y_2$, independently, are hydrogen, halogen, alkyl, alkoxy, nitro, trifluoromethyl, cyano, hydroxy or alkylthio, and
$Y_3$ is hydrogen, alkyl or alkoxy,
in free base form or in pharmaceutically acceptable acid addition salt form thereof to an animal in need of such treatment.

2. A method according to claim 1 wherein the compound is used to treat a spastic condition.

3. A method according to claim 1 wherein the compound is used to relax muscles.

4. A method according to claim 1 wherein the compound is administered at a daily dosage of from 1 to 10 mg.

5. A method according to claim 4 wherein the compound is administered in unit dosage form containing 0.25 to 2 mg of the compound.

6. The method of claim 1, in which the compound is 5-bromo-6-(2-imidozolin-2-yl-amino) quinoxaline.

* * * * *

UNITED STATES PATENT AND TRADEMARK OFFICE
CERTIFICATE OF CORRECTION

PATENT NO. : 4,145,421
DATED : March 20, 1979
INVENTOR(S) : Peter Neumann

It is certified that error appears in the above-identified patent and that said Letters Patent are hereby corrected as shown below:

Col. 1, line 52; change "No. 1,381,479" to --No. 1,381,979--.

Signed and Sealed this

Twentieth Day of November 1979

[SEAL]

Attest:

RUTH C. MASON
Attesting Officer

LUTRELLE F. PARKER
Acting Commissioner of Patents and Trademarks